US007767459B2

(12) United States Patent
Horsti

(10) Patent No.: US 7,767,459 B2
(45) Date of Patent: Aug. 3, 2010

(54) METHOD FOR DETERMINING PROTHROMBIN TIME

(76) Inventor: Juha Horsti, Ylisitarintie 2, Lempaala (FI) FI-37500

( * ) Notice: Subject to any disclaimer, the term of this patent is extended or adjusted under 35 U.S.C. 154(b) by 238 days.

(21) Appl. No.: 11/909,208

(22) PCT Filed: Mar. 20, 2006

(86) PCT No.: PCT/FI2006/050104

§ 371 (c)(1),
(2), (4) Date: Sep. 20, 2007

(87) PCT Pub. No.: WO2006/100346

PCT Pub. Date: Sep. 28, 2006

(65) Prior Publication Data

US 2009/0263903 A1    Oct. 22, 2009

(30) Foreign Application Priority Data

Mar. 21, 2005    (FI) .................................. 20050298

(51) Int. Cl.
*G01N 33/86* (2006.01)
*G01N 33/48* (2006.01)
(52) U.S. Cl. ........................... 436/69; 436/63; 600/369; 73/64.41; 435/13; 422/73
(58) Field of Classification Search .................. 436/63, 436/69; 600/369; 73/64.41; 435/13; 422/73
See application file for complete search history.

(56) References Cited

U.S. PATENT DOCUMENTS

| 4,780,410 | A | * | 10/1988 | Matsuda et al. | ............... 435/7.4 |
| 5,516,640 | A | | 5/1996 | Watanabe et al. | |
| 6,750,053 | B1 | | 6/2004 | Widrig et al. | |
| 6,893,831 | B1 | * | 5/2005 | Kanashima et al. | ......... 435/7.94 |
| 2004/0175296 | A1 | | 9/2004 | Opalsky et al. | |

FOREIGN PATENT DOCUMENTS

EP    0645630 A2    3/1995

OTHER PUBLICATIONS

Hemker et al, Nature of Prothrombin Biosynthesis: Preprothrombinaemia in Vitamin K-Deficiency, Nov. 9, 1963, Nature, vol. 200, No. 4906, pp. 589-590.
Hemker et al, Preprothrombin (complex?) a Circulating Anticoagulant in Coumarin Treated and Vitamin K Deficient Patients, 1964, Thrombos Diathes Haemorrh Suppl, Discussion 14-17, vol. 13, p. 380-391.
Hemker et al, Kinetic Aspects of the Interaction of Blood-Clotting Enzymes: VI. Localization of the Site of Blood-Coagulation Inhibition by the Protein Induced by Vitamin K Absence (PIVKA), 1968, Thrombos Diathes Haemorrh, vol. 20, pp. 78-87.
Stenflo, Vitamin K, Prothrombin and G-Carboxyglutamic Acid, Mar. 17, 1977, New England Journal of Medicine, vol. 296, No. 11, p. 624-626.

Hirsh et al, Oral Anticoagulants: Mechanism of Action, Clinical Effectiveness, and Optimal Therapeutic Range, Nov. 1998, Chest, vol. 114, No. 5, pp. 445-469.
Horsti, Agreement of Owren and Quick Prothrombin Times: Effects of Citrate and Calcium Concentrations and International Sensitivity Index Correction, Nov. 5, 2001, Clinical Chemistry, vol. 47, No. 5, pp. 940-944.
Horsti, Comparison of Quick and Owren Prothrombin Time With Regard to the Harmonisation of the International Normalized Ratio (INR) System, 2002, Clinical Chemistry and Laboratory Medicine, vol. 40, No. 4, pp. 399-403.
Horsti, Has the Quick or the Owren Prothrombin Time Method the Advantage in Harmonization for the International Normalized Ratio System?, 2002, Blood Coagulation and Fibrinolysis, vol. 13, No. 7, pp. 641-646.
Horsti et al, Poor Agreement Among Prothrombin Time International Normalized Ratio Methods: Comparison of Seven Commercial Reagents, 2005, Clinical Chemistry, vol. 51, No. 3, pp. 553-560.
Jackson et all, Has the Time Arrived to Replace the Quick Prothrombin Time Test for Monitoring Oral Anticoagulant Therapy?, Nov. 3, 2005, Clinical Chemistry, vol. 51, No. 3, pp. 483-485.
Hemker et al, Kinetic Aspects of the Interaction of Blood Clotting Enzymes: III. Demonstration of an Inhibitor of Prothrombin Conversion in Vitamin K Deficiency, 1968, Thromb Diath Haemorrh, vol. 19, pp. 346-362.
Kjeldsen et al, Biological Variation of International Normalized Ratio for Prothrombin Times, and Consequences in Monitoring Oral Anticoagulant Therapy: Computer Simulation of Serial Measurements With Goal-Setting for Analytical Quality, 1997, Clinical Chemistry, vol. 43, No. 11, pp. 2175-2182.
Horsti, The Quick and Owren Prothrombin Time Methods for Oral Anticoagulant Therapy Do Not Agree Well Using the International Normalized Ratio (INR) Units, Scandinavian Journal of Clinical and Laboratory Investigation, Letter to the Editor, vol. 63, pp. 1-2, 2003.
Oden et al, Oral Anticoagulation and Risk of Death: A Medical Record Linkage Study, Nov. 9, 2002, BMJ, vol. 325, pp. 1073-1075.
Talstad, Prothrombin Time Standardization by Correction of the Pivka Inhibitor, 1996, Haemostasis, vol. 26, No. 5, pp. 266-275.
Talstad, Why is the Standardization of Prothrombin Time a Problem?, 2000, Haemostasis, vol. 30, No. 5, pp. 258-267.

(Continued)

*Primary Examiner*—Maureen M Wallenhorst
(74) *Attorney, Agent, or Firm*—Brooks Kushman P.C.

(57) ABSTRACT

A method for determining prothrombin time of a plasma or whole blood sample includes measuring prothrombin time for at least two different dilutions for a test sample to determine $t_{min}$ or $INR_{min}$. The prothrombin time for at least two different dilutions for normal plasma is measured to determine $t_{min}$ or $INR_{min}$ values for normal plasma. Next, $t_{Pivka}$ or $INR_{Pivka}$ values are calculated by subtracting the value for normal plasma from the value for the test sample. The Pivka corrected prothrombin time for the test sample is calculated by subtracting $t_{Pivka}$ or $INR_{Pivka}$ from the prothrombin time measured for the test sample.

8 Claims, 3 Drawing Sheets

OTHER PUBLICATIONS

Heckemann et al, Simultaneous Determination of Functional Coagulation Factors and Competitive (PIVKA-) Inhibitors Based on Enzyme Kinetics, 1988, Folia Haematol Leipzig, vol. 115, pp. 533-537.

Henry, Enzyme Inhibitors, 2001, Clinical Diagnosis and Management by Laboratory Methods, Chapter 15, pp. 284-285.

Talstad et al, Simplified Prothrombin Time Standardization, 1994, Haemostasis, vol. 24, No. 1, pp. 4-13.

Talstad, How Does the Pivka Inhibitor Interfere With the One-Stage Prothrombin Time?, 1985, Haemostasis, vol. 15, No. 5, pp. 304-309.

* cited by examiner

METHOD FOR DETERMINING PROTHROMBIN TIME

FIELD OF THE INVENTION

The present invention relates to tests based on INR units for monitoring oral anticoagulation therapy and hepatocellular carcinoma (HCC). Particularly, the invention provides a method for determining prothrombin time of a plasma or whole blood sample taking account the effect which protein induced by vitamin K absence or antagonists (Pivka) has on INR. The object of the invention is to harmonise prothrombin time methods for international normalized ratio (INR) results and also measure Pivka effect as INR units (i.e. $INR_{Pivka}$).

BACKGROUND OF THE INVENTION

The prothrombin time (PT) test was introduced to control oral anticoagulant therapy (OAT), which is used to treat patients with thrombotic disorders such as thrombophilia. This therapy is based on vitamin K antagonists such as warfarin (or coumarin) inhibiting the synthesis of coagulation factors (F II, F VII, F IX and F X) in the liver. Currently, the need for OAT is increasing worldwide. For example, in Finland warfarin medication was prescribed to 1.7% of the population in 2003 and the number of patients is growing due to the ageing population. Since OAT medication needs continuous control to prevent serious consequences of thrombosis or bleeding, it is not surprising that 800 million PT tests are performed each year throughout the world. The most commonly used PT tests are based on Quick's one-stage PT and Owren's method. The latter is most widely used in the Nordic and Benelux countries as well as in Japan, whereas the Quick PT is the approach used elsewhere, accounting for about 95% of all PT tests performed.

When the International Normalised Ratio (INR) and International Sensitivity Index (ISI) were introduced by the World Health Organization (WHO), the aim was to harmonise PT results for oral anticoagulant therapy (5): PT results for a certain plasma or whole blood sample should be the same in INR units regardless of the reagent, instrument or method used. Today each commercial coagulation reagent (i.e. thromboplastin) for PT is calibrated against the primary WHO reference preparation. The results are used to calculate the relative sensitivity of the thromboplastin reagents declared in ISI (International Sensitivity Index). The INR results are then calculated according to the formula: INR=[PT ratio]$^{ISI}$. However, increasing use of the INR format has led to appreciation of its limitations and recently it was found, that the agreement between a number of (or perhaps most) commercial INR methods is poor and clinically too much INR variation was present, thus compromising the good care of the patients (9,10).

Hemker and colleagues (1,2) were the first to characterise the role of protein induced by vitamin K absence or antagonists (Pivka). They discovered that coumarin therapy is associated with an endogenous competitive coagulation inhibitor, which they later named Pivka. The proteins in question were pre-stages of vitamin K-dependent factors. They inhibited the prothrombin-converting complex, presumably against coagulation factor X (FX) (3). It was found that Pivka factors lack gamma carboxyglutamic acid, which is necessary for calcium binding and thereby for "adsorption" of these factors to phospholipid surfaces. Thus, they are inactive analogs to active coagulation factors (4,5).

Talstad contemplates the question why the standardisation of PT is a problem and suggests PT standardization by correction of the Pivka inhibitor (15,16). Heckemann et al. discloses a method for simultaneous determination of functional coagulation factors and competitive Pivka-inhibitors based on enzyme kinetics (17). Moreover, immunochemical assays for Pivka are also known (see, e.g., U.S. Pat. No. 5,516,640). However, no simple and practical method for Pivka correction in PT tests has been introduced in the prior art yet. Consequently, the aim of the present invention was to study the Pivka effect further and compare the Quick and the Owren PT methods in view of Pivka by using different reagents. As a result, the present invention provides a straightforward method for PT testing which overcomes the problem of the Pivka effect.

SUMMARY OF THE INVENTION

The present invention concerns a method for determining a Pivka corrected prothrombin time (PT) comprising the steps of:
a) measuring prothrombin time of at least two different dilutions of a plasma or whole blood sample taken from a patient under oral anticoagulant therapy (OAT) or a patient with hepatocellular carcinoma (HCC) or of a calibrator or control plasma sample in order to determine $t_{min}$ or $INR_{min}$ value for the sample;
b) measuring prothrombin time of at least two different dilutions of a sample of an inhibitor-free plasma or whole blood sample in order to determine $t_{min}$ or $INR_{min}$ value for the normal plasma;
c) calculating $t_{Pivka}$ or $INR_{Pivka}$ value from the results of the steps a) and b);
d) determining the Pivka corrected PT for the sample of step a) by subtracting $t_{Pivka}$ or $INR_{Pivka}$ value obtained in step c) from a prothrombin time measured in step a).

The invention also provides a device, such as a coagulation analyzer or Point of Care instrument (POCT), programmed to perform the method of the invention.

DETAILED DESCRIPTION OF THE INVENTION

The present invention provides a method for determining Pivka effect in INR units and a Pivka corrected prothrombin time (PT) comprising the steps of:
a) measuring prothrombin time of at least two different dilutions of a plasma or whole blood sample taken from a patient under oral anticoagulant therapy (OAT) or a patient with hepatocellular carcinoma (HCC) or of a calibrator or control plasma sample in order to determine $t_{min}$ or $INR_{min}$ value for the sample;
b) measuring prothrombin time of at least two different dilutions of an inhibitor-free plasma or whole blood sample in order to determine $t_{min}$ or $INR_{min}$ value for the normal plasma;

c) calculating $t_{Pivka}$ or $INR_{Pivka}$ value from the results of the steps a) and b);

d) determining the Pivka corrected PT for the sample of step a) by subtracting $t_{Pivka}$ or $INR_{Pivka}$ value obtained in step c) from a prothrombin time measured in step a).

Figure 1:
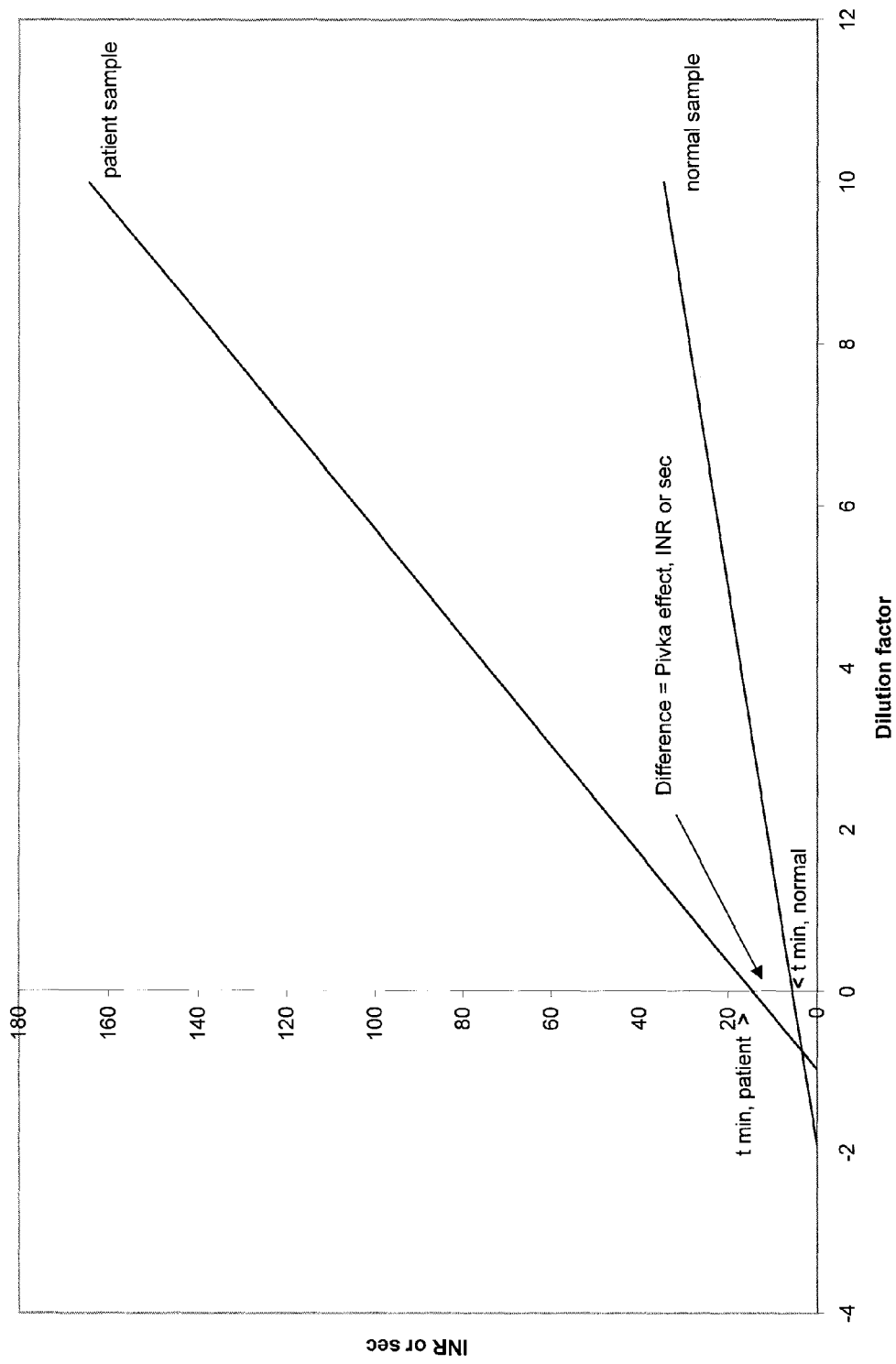
FIG. 1. The model of Pivka calculation. $t_{min}$ value for normal plasma is constant for one reagent lot. $t_{min}$ value for patient plasma is only for one patient. At least two measurements are needed for one patient sample to calculate the line equation.

The $INR_{min}$ or $t_{min}$ value for the samples is obtained by a plot giving the relation between sample dilution or sample volume (X-axis) and clotting time in INR or sec (Y-axis), respectively. A regression line is drawn through the points corresponding to INR's or clotting times of different dilutions or sample volumes of the sample. The regression line intercepts the Y-axis at $INR_{min}$ or $t_{min}$ (see FIG. 1).

Preferably, the value for Pivka effect on the measured prothrombin time is calculated by using the equation:

$$INR_{Pivka} = INR_{min}(\text{patient sample, calibrator, or control}) - INR_{min}(\text{normal plasma})$$

or $$t_{Pivka} = t_{min}(\text{patient sample, calibrator, or control}) - t_{min}(\text{normal plasma}).$$

It is also possible to convert the $t_{Pivka}$ value to the INR units.

In step d) of the method the Pivka effect on the PTs of patient sample is preferably corrected by using one of the following equations:

$$IN_{corrected} = INR_{patient, calibrator, control} - INR_{Pivka}$$

or $$t_{corrected} = t_{patient, calibrator, control} - t_{Pivka}$$

wherein $INR_{patient, calibrator, control}$ or $t_{patient, calibrator, control}$ is a prothrombin time of a sample measured in step a) of the method and wherein $INR_{Pivka}$ or $t_{Pivka}$ is a value calculated in step c) of the method. Preferably said $INR_{patient, calibrator, control}$ or $t_{patient, calibrator, control}$ is a prothrombin time of an undiluted sample, i.e. $INR_{total}$ or $t_{total}$, respectively.

Initial INR values for the PT samples are calculated with the formula of:

$$INR = (\text{sample}_{sec}/\text{normal}_{sec})^{ISI}$$

wherein $\text{sample}_{sec}$ is a prothrombin time of a patient sample (or a calibrator, or a control sample) measured in seconds, $\text{normal}_{sec}$ is a prothrombin time of a sample of normal plasma measured in seconds, and ISI is relative sensitivity of the coagulant reagent used in the PT test. ISI value is usually given by the manufacturer of the reagent or measured using ISI calibrator kits.

The plasma samples for the PT test are preferably diluted with a physiologic salt solution or other suitable buffer. However, when using different sample volumes for the measurement, the sample dilution is not necessary. For the sake of simplicity, these mixes of different sample volumes and test reagents are also called herein as "dilutions". Furthermore, the expression "at least two dilutions" refers herein also to a set of samples wherein one of the samples is an undiluted sample.

Preferably, step b) of the method is performed only once for a certain coagulation reagent (i.e. thromboplastin) and the result obtained is used in step c) for plurality of patient, calibrator, or control samples tested with the same reagent. This is possible since normal plasma does not contain Pivka and, thus, the $t_{min}$ or $INR_{min}$ value of normal plasma is always a constant for a certain coagulation reagent. Preferably, in step b) the inhibitor-free plasma or whole blood sample is taken from a subject known to be healthy (i.e. a sample of normal plasma). The expression "inhibitor-free plasma or whole blood sample" means herein that the plasma or whole blood sample does not contain inhibitors, such as Pivka-inhibitors.

The method of the invention can also be performed with a fully automatic coagulation analyser, since current analysers can easily be programmed to run a sample pattern and calculations required for the execution of the present method. Thus, the present invention is also directed to a device, such as a coagulation analyser or Point of Care instrument (POCT), programmed to perform the method of the invention. Devices and methods for assaying coagulation in fluid samples are well-known in the art (see, e.g., U.S. Pat. No. 6,750,053). Point of Care instruments are portable devices developed for rapid determination of prothrombin time (PT) and INR at locations not limited to laboratories, hospitals or health centers. Patients can, e.g., use Point of Care instruments for self-testing at home.

The present invention is also directed to a use of a device, such as a coagulation analyzer or Point of Care instrument (POCT), for performing the present method.

The present invention is further directed to a device or use of said device, such as a computer, for calculating $t_{Pivka}$ or $INR_{Pivka}$ value from the results of the steps a) and b) of the present method, and determining the Pivka corrected PT for the sample of said step a) by subtracting $t_{Pivka}$ or $INR_{Pivka}$ value obtained in step c) of the present method from a prothrombin time measured in said step a).

EXPERIMENTAL SECTION

Example 1

Materials and Methods

Patients and Blood Sampling

All procedures were approved by our institution's responsible committee in accordance with the Helsinki Declaration of 1975. We analysed normal and OAT patient samples chosen without conscious bias from among hospital and health center patients. Blood (1.8 mL) was drawn from 10 normal and 10 OAT patients into citrate coagulation tubes (Greiner Labortechnik GmbH, Vacuette cat. no. 454322, 9NC) containing 0.2 mL 0.109 mol/L (3.2%) citrate solution. The sample needle (Terumo, Venoject needle, Quick Fit, cat. no. MN-2138MQ) was 0.8×40 mm. Sample tubes were centrifuged at 1850 g for 10 min at 20° C. to separate plasma. All measurements commenced within 8 hours of blood collection at same time.

PT Time Determination

The PT coagulation times were measured using a fully automated BCS coagulation analyser (The Dadebehring Coagulation System, Dadebehring, Marburg, Germany). For the one-stage propthrombin time with Quick, 100 μL of coagulation reagent was added to 50 μL of citrated plasma. The four test reagents were:

(i) Neoplastine CL Plus, cat. no. 00376 (rabbit brain thromboplastin, Diagnostica Stago), lot 031581, ISI 1.30 (no instrument mentioned), ISI values 1.42;

(ii) PT-Fibrinogen Recombinant, cat. no. 20005000 (recombinant rabbit tissue thromboplastin, Instrumentation Laboratory, IL), lot NO 425869, ISI 1.03 for ACL, ISI value 1.08;

(iii) PT-Fibrinogen HS Plus, cat. no. 08469810 (rabbit brain thromboplastin, Instrumentation Laboratory, IL), lot NO325729, ISI 1.13 for ACL, ISI value 1.25;

(iv) Dade Innovin cat. no. B4212-50 (recombinant human tissue thromboplastin, DadeBehring Marburg GmbH), lot 526987, ISI for BCS 0.90, ISI value 1.04.

For the Owren PT (combined thromboplastin reagent) the coagulation reaction contained 10 μL of citrated sample plasma, 50 μL of diluent and 150 μL of reagent. The three test reagents were:

(v) Owren's PT, cat. no. GHI (Global Hemostasis Institute) 131-10 (rabbit brain thromboplastin) containing 25 mmol/L of $CaCl_2$ (cat. no. GHI 155) and a diluent (Owren's buffer, cat. no. GHI 150) from the GHI, lot C414F, ISI 1.09 for optical methods, ISI value 1.17;

(vi) Nycotest PT, cat. no. 1002488 (rabbit brain thromboplastin) and a diluent (Nycotest PT, dilution liquid, cat. no. 1002485) from Axis-Shield as, lot 10107353, ISI 1.13 for Thrombotrack, ISI value 0.95;

(vii) SPA, 50 cat. no. 00105 (tissue thromboplastin) and a diluent (SPA buffer cat. no. 00124) from Diagnostica Stago, lot 022071, ISI 0.98 (no instrument mentioned), ISI value 0.93.

The two methods (4+3 reagents) were calibrated for ISI with the same calibrators Etaloquick cat. no. 00496 from Diagnostica Stago lot 021964.

Plasma dilutions 1:2 were made with a physiologic salt solution (Natriumklorid 9 mg/mL, 500 ml) from Kabi.

Analytical Imprecision of PT Determinations

The within-run imprecision of seven PT tests was measured using one patient plasma sample (n=10 determinations) with an INR value in the therapeutic range, i.e., about 2.2 INR. The respective CVs were: 2.3% for Neoplastine CL Plus, 2.7% for PT-Fibrinogen Recombinant, 1.1% for PT-Fibrinogen HS Plus, 2.6% for Dade Innovin, 1.4% for Owren's PT, 1.6% for Nycotest PT, and 1.0% for SPA.

Pivka Determination and Statistics

We plotted the clotting time (s) on the y-axis and plasma dilution on the x-axis for normal and OAT plasmas. From line equation we got the line intercept at the y-axis, which is the so-called minimal clotting time ($t_{min}$) with an infinite number of clotting factors for one sample (3.11). The difference in intercepts (y-axis) between normal plasma and OAT plasma indicates the action of Pivka in seconds without calibration effect. We calculated the difference in intercepts as INR units (OAT intercept—normal plasma intercept, FIG. 1).

INR results were calculated in seconds using the formula:

$$INR = (sample_{sec}/normal_{sec})^{ISI}$$

The Microsoft Excel 5.0 program was used to obtain the correlation functions and INR results.

Results

The average intercept varies using the Quick PT from 0.03 to 0.14 INR and using the Owren PT 0.01 to 0.03 INR for normal plasmas. The average intercept varies using the Quick PT from 0.40 to 1.46 INR and using the Owren PT 0.20 to 0.28 INR for OAT plasmas. The average SDs of intercepts for normal plasmas (0.07 INR) and OAT plasmas (0.72 INR) using the Quick PT method and the Owren PT were 0.02 INR; 0.23 INR. The average of the Pivka effect on the Quick PT is 0.36 INR (SD 0.43 INR) (without Innovin reagent 0.15 INR; SD 0.14) and on the Owren PT 0.36 INR (SD 0.24 INR). The average INR results from OAT plasmas using Pivka correction were for the Quick PT 2.58 INR (SD 0.11) and for the Owren PT 2.51 (SD 0.16) (Table 1).

Discussion

Harmonisation of INR results is an essential aim in improving patient care and the usefulness of the scientific literature. The therapeutic ranges in INR units for patient care are harmonised and easy for doctors to use. The problem is to unify INR results all over the world, and this is a task for clinical laboratories. In practise laboratories use manufacturer's ISI for an instrument, manufacturer's or "local" (certain country or area) calibrator kits. INR results from same sample should or area none the less be the same. The ISI calibration is in key position in harmonising INR results. The variability of PT reagents (thromboplastin, pH, ionic concentrations and quality, additives etc.) globally is considerable and this makes INR harmonisation very difficult.

PT reagents should have low ISI, near 1.0. For this reason we chose sensitive Owren and Quick reagents for this study. The effect of ISI (calibration) as power function grows in the therapeutic range and at higher INR values (9). This makes result harmonisation more demanding in the therapeutic range. The analytical criteria for PT measurement are very tight (bias≦0.20 INR and CV<5%), partly due to the marked biological variation in OAT patients (12).

Pivka factors have a marked role in the harmonisation of INR results by reason of the effect on calibration in the therapeutic area and the measurement itself. We may observe the Pivka and PT method relationship if we exclude Innovin results (human thromboplastin): the average of Pivka for the Quick PT is 0.15 INR and for the Owren PT 0.36 INR. This means more PIVKA sensitivity and more inhibition (0.21 INR) for the Owren PT method (Table 1). This explains the lower INR results for the Owren compared to the Quick PT (6,13,14). In anticoagulant therapy patients receive more medication (0.21 INR) using Owren PT for care control.

In both methods the same manufacturer, Diagnostica Stago, has reagents with very low Pivka sensitivity. We found the greatest Pivka effect using Innovin (0.98 INR), which reagent contains recombinant human tissue thromboplastin while all other reagents contain thromboplastin of rabbit origin. The Pivka varies using different reagents and is partly thromboplastin-dependent. Intercept SDs for normal and OAT plasmas vary clearly more for the Quick PT (0.03 to 0.14 INR, 0.40 to 1.46 INR) than for the Owren PT (0.01 to 0.03 INR, 0.20 to 0.28 INR) (Table 1). These results confirm our view that using the Owren PT method we can harmonise INR results better globally for different reagents. According to our earlier findings we concluded that Owren PT methods are superior (6,7,8).

In Table 1 we see almost the same results and minimal dispersion between averages of INR results from OAT plasmas minus Pivka inhibition using different PT reagents and methods. This confirms that the Pivka calculations are correct (the same calibration for all reagents). Pivka inhibition causes problems in INR result harmonization globally (calibration, different reagents, instruments and PT methods)(9). ISI calibrators (the higher INR values) from OAT patients contain also Pivka coagulation factors, which complicates INR system. INR values of calibrators should be without Pivka effect.

The method of the present invention needs only at least two PT measurements for one patient sample of different dilutions and simple mathematical calculations. Consequently, the method is easy to adapt to a different kind of instruments. Theoretically PT methods should measure the total effect of anticoagulant drugs on blood coagulation, including active K-dependent clotting factors and inactive factors (Pivka inhibition). This methodological choice means use of Pivka sensitive thromboplastin and method to measure the sum of active and inactive coagulation factors. The another methodological possibility is measure only the active coagulation factors without coagulation inhibitors as in this study. This new method helps to develop the INR system for the best principal possibility to harmonize INRs for oral anticoagulant treatment globally.

Example 2

Materials and Methods

Patients and Blood Sampling

Venous blood samples were obtained from 10 normal subjects and 210 hospital and health-centre patients for whom the PT time test was requested for the monitoring of oral anticoagulant therapy. In our region a "P-INR" test code is used for this purpose. Hence, the patient samples represented all possible phases of anticoagulation: (i) before treatment, (ii) dose-adjusting phase, and (iii) the steady-state phase. All procedures were approved by our institution's responsible committee in accordance with the Helsinki Declaration of 1975. Blood (1.8 mL) was drawn into citrate coagulation tubes (Greiner Labortechnik GmbH, Vacuette cat. no. 454322, 9NC) containing 0.2 mL 0.109 mol/L (3.2%) citrate solution. The sample needle (Terumo, Venoject needle, Quick Fit, cat. no. MN-2138MQ) was 0.8×40 mm. Sample tubes were centrifuged at 1850 g for 10 min at 20° C. to separate plasma. All measurements were commenced within 8 hours of blood collection.

PT Determination

The PT coagulation times were measured using a fully automated BCS coagulation analyser (DadeBehring Coagulation System, DadeBehring, Marburg, Germany).

For the one-stage prothrombin time with Quick, 100 µL of coagulation reagent was added to 50 µL of citrated plasma and for the dilution sample volumes were 100 µL+25 µL+25 µL (a physiologic salt solution, "Natriumklorid 9 mg/mL", 500 ml from Kabi). The test reagent was: Dade Innovin cat. no. B4212-50 (recombinant human tissue thromboplastin, DadeBehring Marburg GmbH), lot 536928, ISI=0.92.

For the Owren PT (combined thromboplastin reagent) the coagulation reaction contained 10 µL of citrated sample plasma, 60 µL of diluent and 140 µL of reagent and volumes for "dilution measurement": 5 µL+65 µL+140 µL, 7 µL+63 µL+140 µL or 14 µL+56 µL+140 µL. The test reagent was: Nycotest PT, cat. no. 1002488 (rabbit brain thromboplastin) and a diluent (Nycotest PT, dilution liquid, cat. no. 1002485) from Axis-Shield as, lot 10112954, ISI=1.07.

ISI Calibration

Two local ISI calibrator kits were used: (i) "Svensk nationell kalibrator för protrombinkomplexaktiviet", from Equalis, lot 11, 12, Cal 1=0.85 INR and Cal 2=3.19 INR (used mainly in Sweden and Norway). (ii) "ISI-kalibraattorikitti", cat. no. B10000150, from Bioclin, lot 8, Cal 1=2.07 INR, Cal 2=3.52 INR and Cal 3=1.0 INR (used mainly in Finland).

Further, two commercial (manufacturer calibration) ISI calibration kits were used: (i) Etaloquick cat. no. 00496 from Diagnostica Stago lot 041555. Cal 1=0.91 INR, Cal 2=3.24 INR and Cal 3=4.90 INR. (ii) PT-Multi Calibrator cat. no. OPAT 035 from DadeBehring lot 35422. Cal 1=1.01 INR, Cal 2=1.30 INR, Cal 3=1.65 INR, Cal 4=2.97 INR, Cal 5=4.00 INR, Cal 6=5.29 INR.

Determination of Minimal PT Time and Respective INR

The procedure for measuring the inhibition in seconds was conducted essentially as described by Hemker and co-workers (1,2,3). We constructed PT (sec) versus D (D=plasma or calibrator dilution factor) plots for normal and OAT plasmas as well as for different calibrators. This is consistent with an uncompetitive inhibition principle with oral anticoagulants (18). From the line equation the y-axis intercept is calculated. This is the so-called minimal clotting time ($t_{min}$) with an infinite number of clotting factors (3). The difference in intercepts (y-axis) between normal plasma and OAT plasma indicates the action of PIVKA in seconds without calibration effect. We furthermore calculated the difference in intercepts also in INR units and subtracted it from total INR:

$$INR_{Corrected} = INR_{Total} - INR_{Pivka}$$

INR's were calculated using the formula: $INR=(sample_{sec}/normal_{sec})^{ISI}$ The dilution factors for the Quick PT linearity check were: 0.91; 1.00; 1.25; 1.67 2.00 and the Owren PT linearity check were: 0.67; 1.00; 1.25; 1.67; 2.50.

Analytical Imprecision and Statistics

The within-run precision of PT tests was measured using one patient plasma sample (n=10 determinations) with an INR value in the therapeutic range, i.e., approx. 2.2 INR. The respective CVs were: 2.6% for Dade Innovin, 1.6% for Nycotest PT. This is consistent with our previous observations with a broader spectrum of reagents (9). The Microsoft Excel 5.0 program was used to obtain the correlation functions and INR results by using the least-squares fit.

Results

PIVKA inhibition was demonstrable in all calibrators with INR values greater than 1. As expected, the inhibition increased together with the increase in calibrator INR value (Table 2). It is noteworthy, however, that the PIVKA inhibition varied among the calibrator kits and was different for the two different PT methods.

We further demonstrated that there was a conspicuous difference in INR results in the case of 200 OAT patients, depending on the PT method, even if the same calibrator was used. The average for traditional INR was 3.89 and 2.68 when determined by the Quick and Owren method, respectively. After PIVKA correction the averages were 2.49 and 2.30 INR units, representing $INR_{Corrected}$. These results allowed us to estimate the target point of 2.13 $INR_{Corrected}$ units, the range being 1.6-2.6 $INR_{Corrected}$ units.

Figure 2:
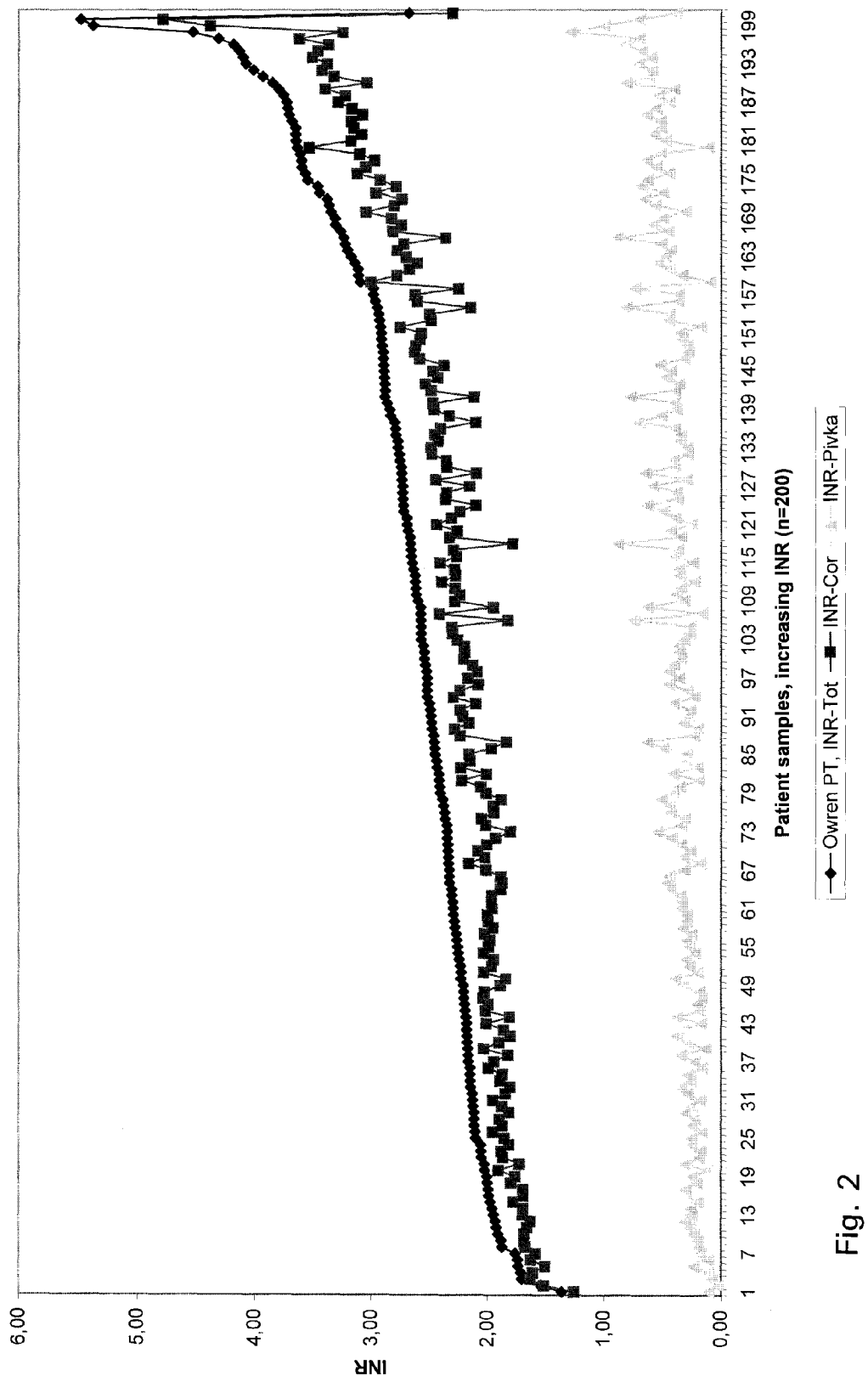
FIG. 2. Traditional INR ($INR_{Total}$) determined by Owren PT, active coagulation factors ($INR_{Corrected}$) and inhibition effect ($INR_{Pivka}$) for 200 OAT patient plasmas in increasing order using Etaloquick calibration.
Figure 3:
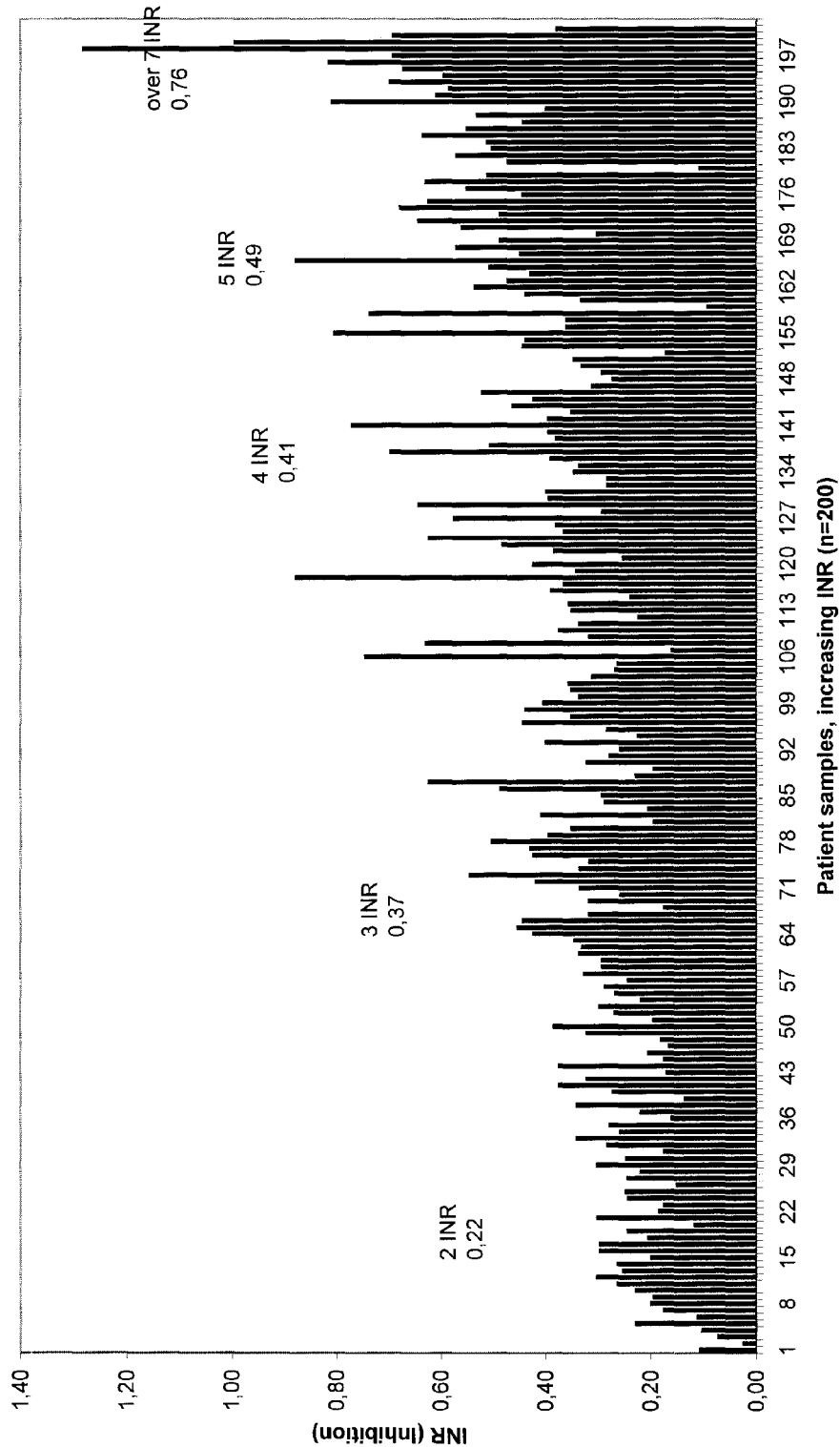
FIG. 3. PIVKA inhibition (inhibitory factors FII, FVII and FX) on Owren PTs in 200 OAT patient samples as INR units.

The linearity using different dilutions was good for the Quick and Owren PT methods. We further demonstrated that there was a difference—increasing towards higher INR values—between the traditional PT measurement and the new method measuring the active coagulation ($INR_{Corrected}$) in the case of the 200 OAT patients. Individual original and corrected ($INR_{Corrected}$) values are illustrated in FIG. 2. The individual variation in coagulation inhibition is notable at different INR levels (Owren PT) for OAT patient samples as illustrated in FIG. 3.

Discussion

This new method requires two PT measurements for one patient sample and mathematical calculations: $INR_{patient, calibrator, or control} - INR_{Pivka} = INR_{Corrected}$. It is easy to adapt for different kinds of instruments. The reagent costs are the same using a half volume for PT measurements, as automation instruments can pipet very low liquid volumes.

TABLE 1

Measuring Pivka inhibition using the Quick and Owren PT methods and different reagents for both methods.

| Etaloquick calibration | Average equation of normal plasma (s), n = 10 | Intercept SD of normal plasma (INR) | Average equation of OAT plasma (s), n = 10 | Intercept SD of OAT plasma (INR) | Pivka (INR) | Average of OAT plasma | Average of OAT plasma minus Pivka |
|---|---|---|---|---|---|---|---|
| The Quick PT ||||||||
| Innovin | y = 2.92x + 5.63 | 0.05 | y = 15.05x + 14.53 | 0.59 | 0.98 | 3.41 | 2.43 |
| PT Fibrinogen Recomb | y = 8.37x + 7.53 | 0.14 | y = 32.59x + 10.46 | 1.46 | 0.19 | 2.88 | 2.69 |
| PT Fibrinogen HS Plus | y = 7.45x + 8.48 | 0.03 | y = 25.98x + 12.56 | 0.41 | 0.27 | 2.87 | 2.60 |
| Neoplastin | y = 9x + 4.42 | 0.07 | y = 27.66x + 3.84 | 0.40 | −0.02 | 2.62 | 2.64 |
| Average |  | 0.07 |  | 0.72 | 0.36 | 2.95 | 2.59 |
| SD |  |  |  | 0.43 | 0.33 |  | 0.11 |
| The Owren PT ||||||||
| SPA | Y = 9.15x + 13.37 | 0.03 | y = 52.58x + 15.58 | 0.21 | 0.09 | 2.78 | 2.69 |
| Nycotest PT | y = 8.7x + 11.98 | 0.02 | y = 44.63x + 21.84 | 0.20 | 0.44 | 2.93 | 2.49 |
| Owren PT | Y = 8.76x + 15.98 | 0.01 | y = 35.8x + 28.69 | 0.28 | 0.56 | 2.92 | 2.36 |
| Average |  | 0.02 |  | 0.23 | 0.36 | 2.88 | 2.51 |
| SD |  |  |  |  | 0.24 | 0.09 | 0.16 |

TABLE 2

INR inhibition obtained with four calibrator kits using two different PT methods

| Calibrator[a] | Calibrator INR[b] | Quick PT | | | Owren PT | | |
|---|---|---|---|---|---|---|---|
| | | INR inhibition[c] | INR[d] cor | Inhibition (%) | INR inhibition[c] | INR[d] cor | Inhibition (%) |
| Multical 1 | 1.01 | 0.00 | 1.01 | None | 0.00 | 1.01 | None |
| Multical 2 | 1.30 | 0.13 | 1.17 | 10.07 | 0.04 | 1.26 | 3.29 |
| Multical 3 | 1.66 | 0.27 | 1.39 | 16.09 | 0.11 | 1.55 | 6.76 |
| Multical 4 | 2.93 | 0.70 | 2.23 | 23.86 | 0.29 | 2.64 | 9.74 |
| Multical 5 | 4.14 | 1.14 | 3.00 | 27.53 | 0.49 | 3.65 | 11.90 |
| Multical 6 | 5.46 | 1.85 | 3.61 | 33.91 | 1.12 | 4.34 | 20.43 |
| Etaloquick 1 | 1.00 | 0.00 | 1.00 | None | 0.00 | 1.00 | None |
| Etaloquick 2 | 2.85 | 0.63 | 2.22 | 22.13 | 0.31 | 2.54 | 10.78 |
| Etaloquick 3 | 4.25 | 1.16 | 3.09 | 27.24 | 1.00 | 3.25 | 23.59 |
| Bioclin 3 | 1.00 | 0.00 | 1.00 | None | 0.00 | 1.00 | None |
| Bioclin 1 | 2.07 | 0.12 | 1.95 | 5.78 | 0.32 | 1.75 | 15.36 |
| Bioclin 2 | 3.52 | 0.80 | 2.72 | 22.86 | 0.74 | 2.78 | 21.10 |
| Equalis 1 | 0.85 | 0.00 | 0.85 | None | 0.00 | 0.85 | None |
| Equalis 2 | 3.19 | 0.28 | 2.91 | 8.78 | 0.31 | 2.88 | 9.69 |

[a]Arranged according to increasing INR values.
[b]As given by the manufacturer.
[c]We constructed INR (y-axis) versus C (C = calibrator dilution factor) (x-axis) plots for each calibrator. The inhibition was calculated by subtracting, in turn, the y-axis intercept (INR) value of each respective calibrator of the lowest INR value from calibrators with higher values, i.e., containing PIVKA. For details, see Materials and Methods and FIG. 1.
[d]Represents the y-axis intercept of the INR versus 1/C line, i.e., the hypothetical clotting time or $INR_{Corrected}$ with no inhibitors present.

REFERENCES

1. Hemker H C, Veltkamp J J, Hensen A, Loeliger E A. Nature of Prothrombin Biosynthesis: Preprothrombinemia in Vitamin K-deficiency. Nature 1963; 200:590-8.
2. Hemker HC. Preprothrombin (complex?) a circulating anticoagulant in coumarin treated and vitamin K deficient patients. Thrombos Diathes Haemorrh Suppl 1964; 13:380.
3. Henker H C, Muller A D. Kinetic Aspects of the Interaction of Blood-Clotting Enzymes. VI. Localization of the Site of Blood-Coagulation Inhibition by the Protein Induced by Vitamin K Absence (PIVKA). Thrombos Diathes Haemorrh 1968; 20:78-87.
4. Stenflo J. Vitamin K, prothrombin and g-carboxyglutamatic acid. New Eng J Med 1977; 296:624.
5. Hirsh J, Dalen J E, Anderson D R, Poller L, Bussey H, Ansell J et al. Oral Anticoagulants Mechanism of Action, Clinical Effectiveness, and Optimal Therapeutic Range. Chest 1998; 114:445-69.
6. Horsti J. Agreement of Owren and Quick Prothrombin Times: Effects of Citrate and Calcium Concentrations and International Sensitivity Index Correction. Clin Chem 2001; 47:940-4.
7. Horsti J. Comparison of Quick and Owren Prothrombin Time with Regard to the Harmonisation of the International Normalised Ration (INR) System. Clin Chem Lab Med 2002; 40:399-403.
8. Horsti J. Has Quick or Owren prothrombin time method the advantage in harmonisation for the International Normalized Ratio system? Blood Coag Fibriol 2002; 13:641-6.
9. Horsti J, Uppa H, Vilpo J. Poor agreement between different prothrombin time International Normalized Ratio (INR) methods: comparison of seven commercial reagents. Clin Chem 2005; 51:553-60.

10. Jackson C M, Esnouf M P. Has the Time Arrived to Replace the Quick Prothrombin Time Test for Monitoring Oral Anticoagulant Therapy. Clin Chem 2005; 51:483-5.
11. Hemker H C, Veltkamp J J, Loeliger E A. Kinetic aspects of the interaction of blood clotting enzymes.3. Demonstration of an inhibitor of prothrombin conversion in vitamin K deficiency. Thromb Diath Haemorrh. 1968; 19:346-63.
12. Kjeldsen J, Lassen J F, Petersen P H, Brandslund I. Biological variation of International Normalised Ratio for prothrombin times, and consequences in monitoring oral anticoagulant therapy: computer simulation of serial measurements with goal-setting for analytical quality. Clin Chem 1997; 43:2175-82.
13. Horsti J. The Quick and Owren prothrombin time methods for oral anticoagulant therapy do not agree well using the International Normalized Ratio (INR) units. Scand J Clin Lab Invest 2003; 63:455-6.
14. Odén A, Fahlén M. Oral anticoagulation and risk of death: a medical record linkage study. BMJ 2002; 325:1073-5.
15. Talstad I. Prothrombin time standardization by correction of the Pivka inhibitor. Haemostasis 1996; 25(5):266-275.
16. Talstad I. Why is the standardization of prothrombin time a problem? Haemostasis 2000; 30(5):258-267.
17. Heckemann H. -J., Ruby Ch. and Rossner K. Simultaneous Determination of Functional Coagulation Factors and Competitive (PIVKA-) Inhibitors Based on Enzyme Kinetics. Folia Haematol., Leipzig 1988; 115(4):533-537.
18. Henry J B. Clinical Diagnosis and Management by Laboratory Methods. 20th ed. Philadelphia: W.B. Saunders Company, 2001:284-5.

The invention claimed is:

1. A method for determining protein induced by vitamin K absence or antagonists (Pivka)-corrected prothrombin time (PT) comprising the steps of:
   a) measuring prothrombin time of at least two different dilutions of a plasma or whole blood sample taken from a patient under oral anticoagulant therapy (OAT) or a patient with hepatocellular carcinoma (HCC) or of a calibrator or control plasma sample in order to determine $t_{min}$ or $INR_{min}$ value for the sample, $t_{min}$ being a y-intecerpt of a plot of clotting time versus dilution factor and $INR_{min}$ being a y-intercept of a plot of clotting time (t) versus international normalised ratio (INR), the sample including Pivka;
   b) measuring prothrombin time of at least two different dilutions of Pivka-free plasma or whole blood sample in order to determine $t_{min}$ or $INR_{min}$ value for the Pivka-free plasma or whole blood;
   c) calculating $t_{Pivka}$ or $INR_{Pivka}$ value from the results of the steps a) and b), $t_{Pivka}$ being the effect of Pivka on clotting time calculated by subtracting $t_{min}$ for the Pivka-free plasma or whole blood from the $t_{min}$ value for the sample in step a) and $INR_{Pivka}$ being the effect of Pivka on INT calculated by subtracting $INR_{min}$ for the Pivka-free plasma or whole blood from the $INR_{min}$ value for the sample in step a); and
   d) determining the Pivka corrected PT for the sample of step a) by subtracting the $t_{Pivka}$ or $INR_{Pivka}$ value obtained in step c) from a prothrombin time measured in step a).

2. The method according to claim 1, wherein the Pivka corrected PT for the sample of step a) is determined in step d) by using one of the following equations:

$$INR_{corrected} = INR_{patient, calibrator, control} - INR_{Pivka}$$

or $$t_{corrected} = t_{patient, calibrator, control} - t_{Pivka}$$

wherein $INR_{patient, calibrator, control}$ or $t_{patient, calibrator, control}$ is a PT of a sample measured in step a) of the method, and wherein $INR_{Pivka}$ or $t_{Pivka}$ is a value calculated in step c) of the method.

3. The method according to claim 1, wherein it is performed with a fully automatic coagulation analyser programmed to run a sample pattern and calculations required for the execution of the method.

4. The method according to claim 1, wherein step b) is performed once for a coagulation reagent and the result obtained is used in step c) for a plurality of patient, calibration or control samples tested with the same reagent.

5. The method of claim 4 wherein the coagulation reagent comprises thromboplastin.

6. A device programmed for performing a method for determining vitamin K absence or antagonists (Pivka)-corrected prothrombin time (PT), the method comprising:
   a) measuring prothrombin time of at least two different dilutions of a plasma or whole blood sample taken from a patient under oral anticoagulant therapy (OAT) or a patient with hepatocellular carcinoma (HCC) or of a calibrator or control plasma sample in order to determine $t_{min}$ or $INR_{min}$ value for the sample, $t_{min}$ being a y-intercept of a plot of clotting time versus dilution factor and INRmin being a y-intercept of a plot of clotting time (t) versus international normalised ratio (INR), the sample including Pivka;
   b) measuring prothrombin time of at least two different dilutions of Pivka-free plasma or whole blood sample in order to determine $t_{min}$ or $INR_{min}$ value for the Pivka-free plasma or whole blood;
   c) calculating $t_{Pivka}$ or $INR_{Pivka}$ value from the results of the steps a) and b), $t_{Pivka}$ being the effect of Pivka on clotting time calculated by subtracting $t_{min}$ for the Pivka-free plasma or whole blood from the $t_{min}$ value for the sample in step a) and $INR_{Pivka}$ being the effect of Pivka on INT calculated by subtracting $INR_{min}$ for the Pivka-free plasma or whole blood from the $INR_{min}$ value for the sample in step a); and
   d) determining the Pivka corrected PT for the sample of step a) by subtracting the $t_{Pivka}$ or $INR_{Pivka}$ value obtained in step c) from a prothrombin time measured in step a).

7. The device of claim 6, wherein said device comprises a coagulation analyzer or Point of Care instrument (POCT).

8. The device of claim 6, wherein said device comprises a computer.

* * * * *